United States Patent [19]

Edwards et al.

[11] Patent Number: 5,555,908
[45] Date of Patent: Sep. 17, 1996

[54] VALVED PRN ADAPTER FOR MEDICAL ACCESS DEVICES

[75] Inventors: Floyd V. Edwards, Clarence, N.Y.; Douglas P. Orr, Sandy, Utah

[73] Assignee: Becton, Dickinson and Company, Franklin Lakes, N.J.

[21] Appl. No.: 494,133

[22] Filed: Jun. 23, 1995

[51] Int. Cl.⁶ .................................................. F16K 15/18
[52] U.S. Cl. ..................... 137/329.1; 251/149.6; 251/149.8
[58] Field of Search ............................. 251/149.1, 149.6, 251/339, 149.8; 137/614.19, 614.05, 329.1, 329.4

[56] References Cited

U.S. PATENT DOCUMENTS

| | | | |
|---|---|---|---|
| 4,123,089 | 10/1978 | Viero et al. | 137/329.1 X |
| 4,190,075 | 2/1980 | Kayser | 137/329.1 |
| 4,527,587 | 7/1985 | Fairlamb | 251/149.6 X |
| 5,085,645 | 2/1992 | Purdy et al. | |
| 5,108,380 | 4/1992 | Herlitze et al. | |
| 5,236,005 | 8/1993 | Berg | 137/329.1 X |
| 5,251,873 | 10/1993 | Atkinson et al. | |
| 5,269,771 | 12/1993 | Thomas et al. | |

Primary Examiner—Kevin Lee
Attorney, Agent, or Firm—Arthur D. Dawson

[57] ABSTRACT

A valved adapter for connecting a fluid handling device to a medical device includes a body with a longitudinal axis and having a female luer fitting at a proximal end, a distal end and a passageway therethrough. The passageway has a chamber intermediate the proximal end and the distal end containing a valve having a normally closed position but operative to an open position. The valve includes a relatively elongate resilient member with a proximal end and an axis substantially coaxial to the longitudinal axis of the adapter. The valve further includes a pusher disposed at the proximal end of the elongate resilient member. The pusher includes a telescopic portion having an extended position and a collapsed position. The telescopic portion is biased to the extended position.

22 Claims, 10 Drawing Sheets

VALVED PRN ADAPTER FOR MEDICAL ACCESS DEVICES

FIELD OF INVENTION

The present invention relates to medical access devices and more particularly to a valved adapter useful with a variety of medical access devices.

BACKGROUND

Medical access devices, particularly infusion devices, over-the-needle catheters, other catheters and feeding tubes are important tools for administration of fluids to patients. After placement, in normal management of a catheter or other medical access device in a patient, it is often necessary to be able to add or withdraw fluids through the device. In many surgical procedures, it is routine to place an intravenous catheter so that if it is necessary to medicate a patient during a procedure, the catheter already is in place. In other types of procedures it is necessary to administer medicaments periodically through the device or to withdraw samples. In all of these applications, the presence of a valve mechanism on the device to facilitate the addition of the medicament and to close the device after the addition is desirable.

The need for valved closures on medical access devices has been addressed in several patents. U.S. Pat. No. 5,085,645 teaches an over-the-needle catheter having an integral valve in a passage in the catheter hub. The patent discloses a valved adapter that is an integral part of a catheter hub.

U.S. Pat. No. 5,251,873 teaches a medical coupling site that is adapted to be attached directly to a standard male luer lock fitting. The coupling site includes a valve element contained within a tubular retainer. The coupling site includes a slit rubber diaphragm valve that is deflected by introduction of a male luer fitting and closes by the removal of the male luer. According to international standards, there is an allowable range of 2.5 mm in engagement length of a luer fitting. This variation in engagement length occurs because of variation in the outside diameter of the male projection and the inside diameter of the female receptacle of the luer fittings. Thus, a "fat" male luer will result in a "short" engagement length and conversely. Valves of the type disclosed in U.S. Pat. No. 5,251,873 may not open fully with male luer fittings at the "short" end of the allowable dimension, and since they also depend on the diaphragm for sealing around the male luer tip, they may also leak when a male fitting is mounted or may not fully close once opened.

U.S. Pat. No. 5,108,380 discloses a valve device for a hub member of a catheter. The valve is actuated by the placement of a male luer fitting which displaces a piston biased by a coil spring to open the valve.

U.S. Pat. No. 5,269,771 discloses a needleless introducer with a hem, static valve. The valve mechanism includes a plunger biased by a coil spring which, upon actuation, spreads a pair of resilient valve elements. This design may not be fully opened by a male luer fitting at the "short" side of the dimension, and the sealing depends upon the resilient valve elements closing against themselves. Further, the valve disclosed in U.S. Pat. No. 5,269,771 is composed of several different materials and is complex to assemble.

Additionally, U.S. application Ser. No. 08/288,170 which is commonly assigned to the assignee of the present disclosure teaches a valved adapter for a medical access device that includes a pusher for opening the valve with a proximal surface forming a substantially continuous surface with the proximal surface of the adapter when the valve is closed, Valves and adapters of the type described above fall into a medical device category often referred to as "PRN" from the Latin pro re nata, i.e., as the circumstances may require. A typical example of usage for this type of device might be on a catheter left in place for three days. During this three day usage duration, a bolus dosage of a medicament might be given every 4 hours using a protocol including at each dosage interval: a) flushing the catheter to check patency; b) administration of the medicament; and c) flushing the medicament from the catheter with heparin or saline. During this typical usage period, this protocol results in 54 operations of the valve, i.e., 6 times a day, 3 steps each time and 3 days. In between each dosage the valve must not leak, and it must be readily reopened. Previously, the bolus introduction may have been made using hypodermic needles penetrating a resilient septum. However, a septum may start leaking after multiple penetrations with a sharp needle. Because of this leakage potential and the concerns about risks to practitioners and service personnel from "sharps", hospitals have changed many protocols to reduce the use of pointed hypodermic needles. The PRN adapters as described above have been developed to address the hospitals' changing needs.

While the teachings cited above address many of the practitioners' concerns, there is still a need for a valved adapter for medical access devices that offers rapid, easy-to-use access with automatic positive on/off flow control. Devices such as disclosed above generally depend upon the placement of a male luer fitting of a fluid handling device onto a female luer fitting of the adapter to open the valve with the removal of the male luer fitting allowing the valve to close. Users of many of these devices have become aware that, since the valve in the adapter generally closes as the male luer fitting is removed, the closure of the valve often causes a small fluid discharge or "spurt" of fluid from the adapter. Because of the well documented concerns regarding fluid borne pathogens, such uncontrolled discharges are most undesirable.

Another problem noted in currently available adapters, that have a valve that closes as the male luer fitting is removed, is termed "backflow". As an example, a syringe with a male luer is used to deliver a fluid into an adapter mounted on a venous catheter. When the contents of the syringe are expelled, a continuous liquid column exists from the syringe to the open end of the catheter in the blood vessel. When the syringe is removed, the volume of the liquid column present in the syringe tip is removed from the column resulting in a like volume of blood being drawn back into the catheter. This "backflow" blood may clot and cause blockage in a subsequent use of the catheter.

Thus, while there are many forms of adapters available, there is still a need for an adapter which substantially prevents uncontrolled fluid discharges from adapters and backflow into catheters attached to adapters as fluid handling devices are dismounted. Additionally, some of the currently available adapters are open at the proximal end requiring an additional plug or cover to avoid contamination of the fitting when a fluid delivery device is not mounted. A device having these features plus the advantage of being self closing and easily cleanable is disclosed herein below.

SUMMARY

A valved adapter for connecting a fluid handling device to a medical device includes a body having a longitudinal axis with a proximal end with a female luer fitting, a distal end and a passageway therethrough. The passageway has a chamber intermediate the first end and the second end. The adapter includes a valve having a normally closed position and an open position contained within the chamber, the valve including a relatively elongate resilient member having a proximal end with an axis substantially coaxial to the longitudinal axis of the adapter. The valve further includes a pusher disposed at the proximal end of the elongate resilient member. The pusher includes a telescopic portion with an extended position and a collapsed position that preferably is biased to the extended position.

The adapter of the present invention, by having a pusher with a telescopic portion, substantially eliminates the tendency of many valved adapters to spurt liquid present on the surface of the pusher portion as the fluid handling device is removed, because the telescopic portion allows the male luer fitting to substantially obstruct the passageway while the valve is fully closed. The telescopic portion also allows the user to more easily control the dismounting of the fluid handing device. Since the valve of the adapter is already fully closed before the device is fully removed, there is little probability of spurting and of backflow. Valves in devices in accordance with the teachings of the cited patents are partially open as long as a fluid handling device is partially mounted, making it necessary to fully dismount the fluid handling device as rapidly as possible. The preferred adapter of the present invention has an easily cleaned proximal surface which may be wiped substantially clean by a user when the fluid handling device is removed. Further, since the valve is opened by the compression of the resilient member, the adapter of the present invention is tolerant of variations in the diameter of the male luer fitting within the range allowable by international standards and is capable of withstanding repeated cycles of mounting and dismounting of fluid handling devices.

BRIEF DESCRIPTION OF THE DRAWING

FIG. 6b is an alternate embodiment of the portion of the proximal end from Fig, 6a;

FIG. 6c is another alternate embodiment of the portion of the proximal end from Fig, 6a;

DETAILED DESCRIPTION

While this invention is satisfied by embodiments in many different forms, there is shown in the drawings and will herein be described, several embodiments of the invention with the understanding that the present disclosure is to be considered descriptive of the principles of the present invention and is not intended to limit the scope of the invention to the embodiments illustrated. The scope of the invention will be measured by the appended claims and their equivalents, In this description, the term "proximal" refers to the end of the adapter closest to the user, with the term "distal" referring to the end of the adapter away from the user, Referring to FIGS. 1–6, a preferred valved adapter 10 of the present invention for connecting a fluid handling device 12 to a medical device includes a body 16 with a longitudinal axis A having a proximal end 20 preferably having a female luer fitting 22, a distal end 24 and a passageway 28 therethrough. Passageway 28 includes a chamber 30 intermediate proximal end 20 and distal end 24.

Figure 1:
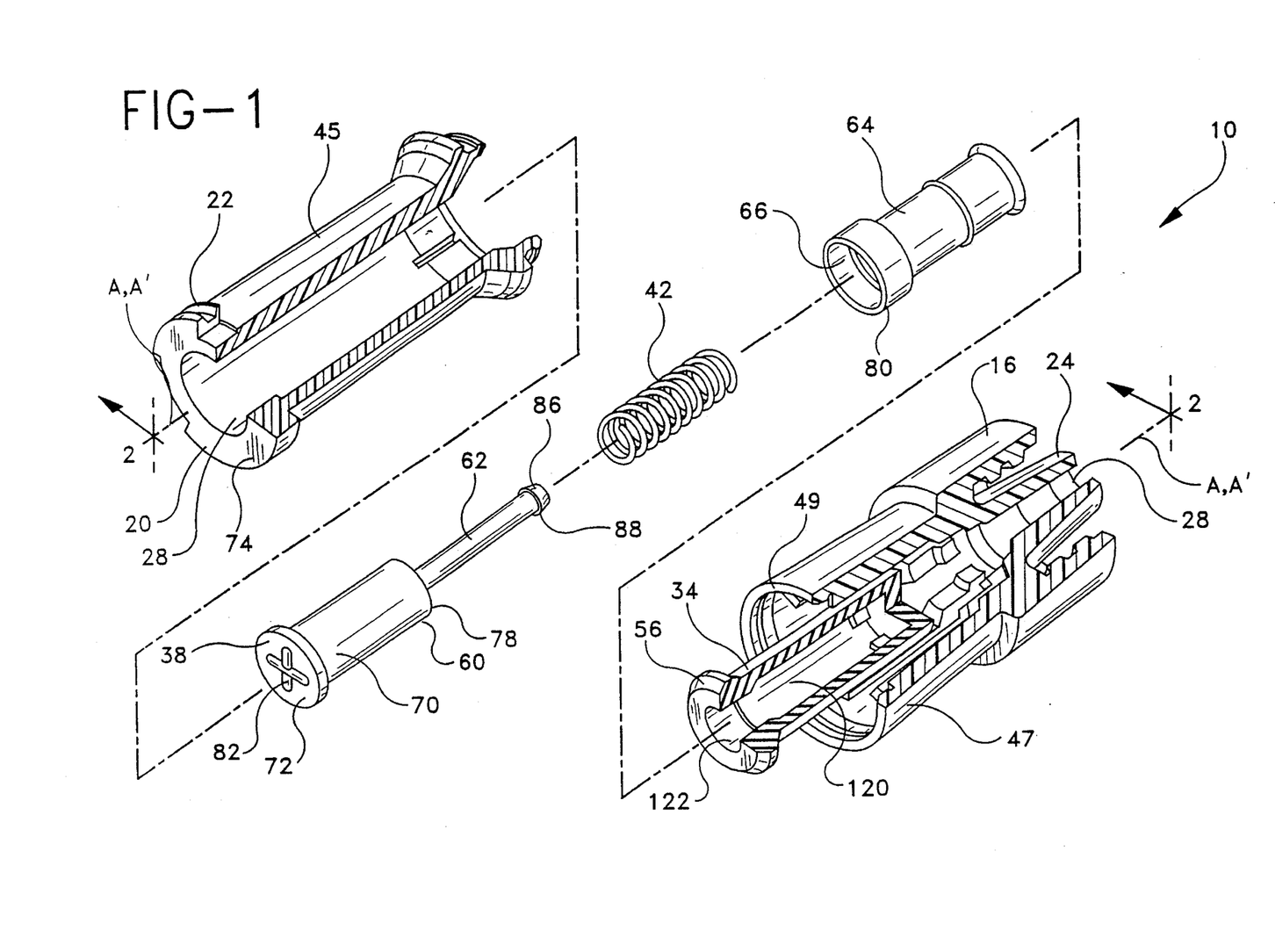
FIG. 1 is an exploded cutaway perspective view of a preferred embodiment of the valved adapter of the present invention.
Figure 2:
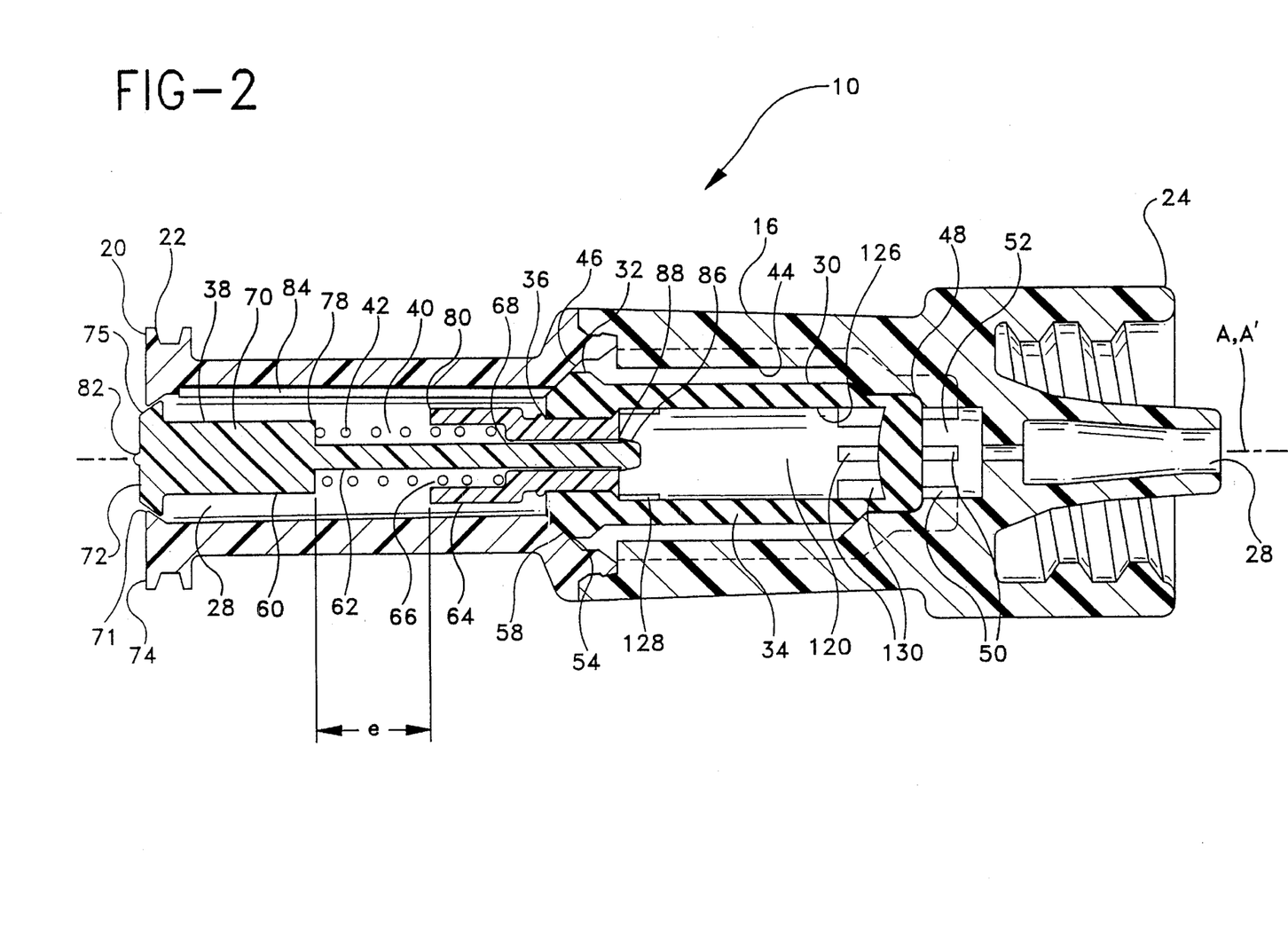
FIG. 2 is a schematic cross-sectional view of the embodiment of FIG. 1 along the line 2—2.
Figure 3:
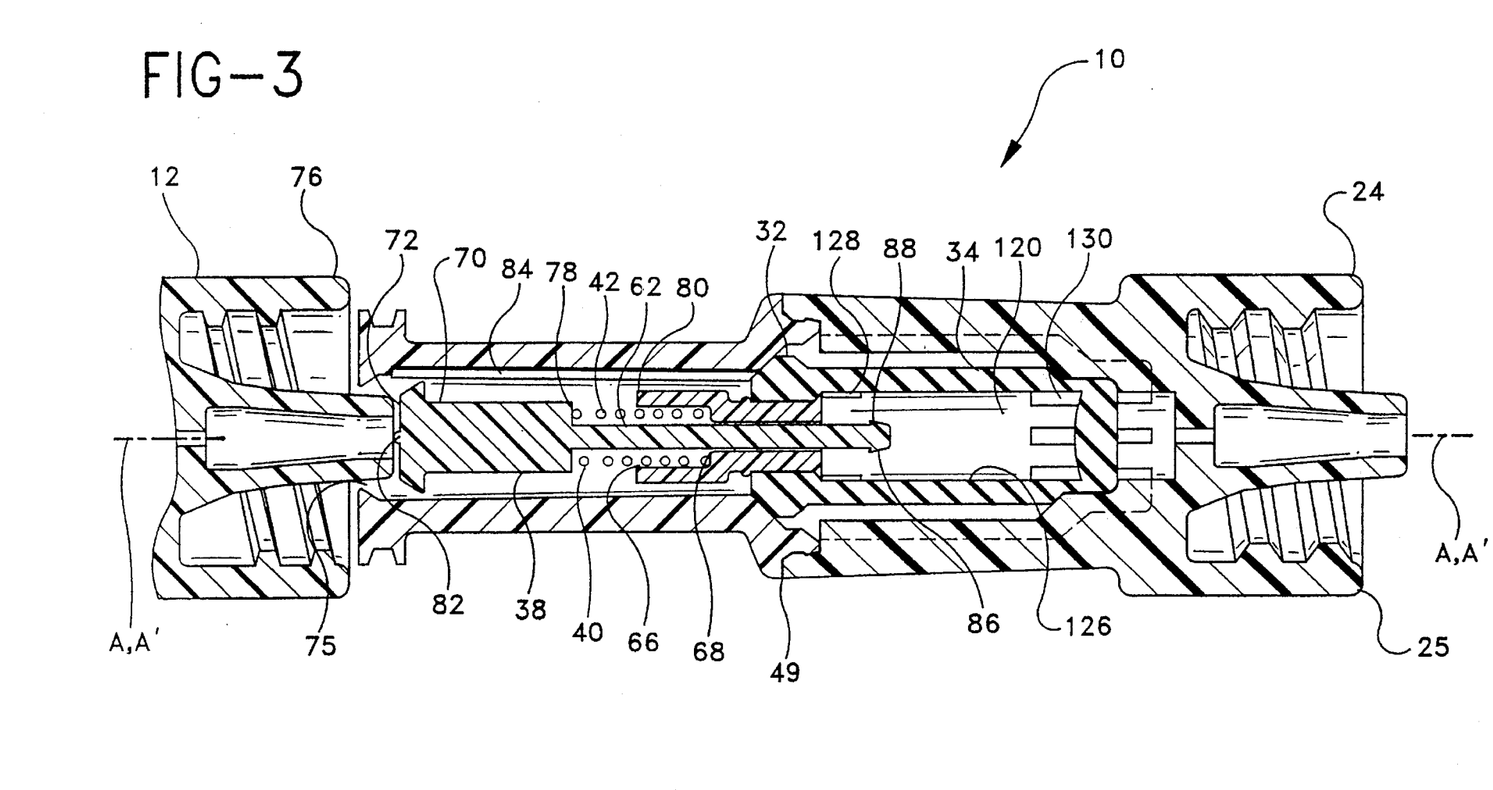
FIG. 3 is a schematic cross-sectional view of the adapter illustrated in FIG. 2 with a fluid handling device partially mounted on the proximal end.
Figure 4:
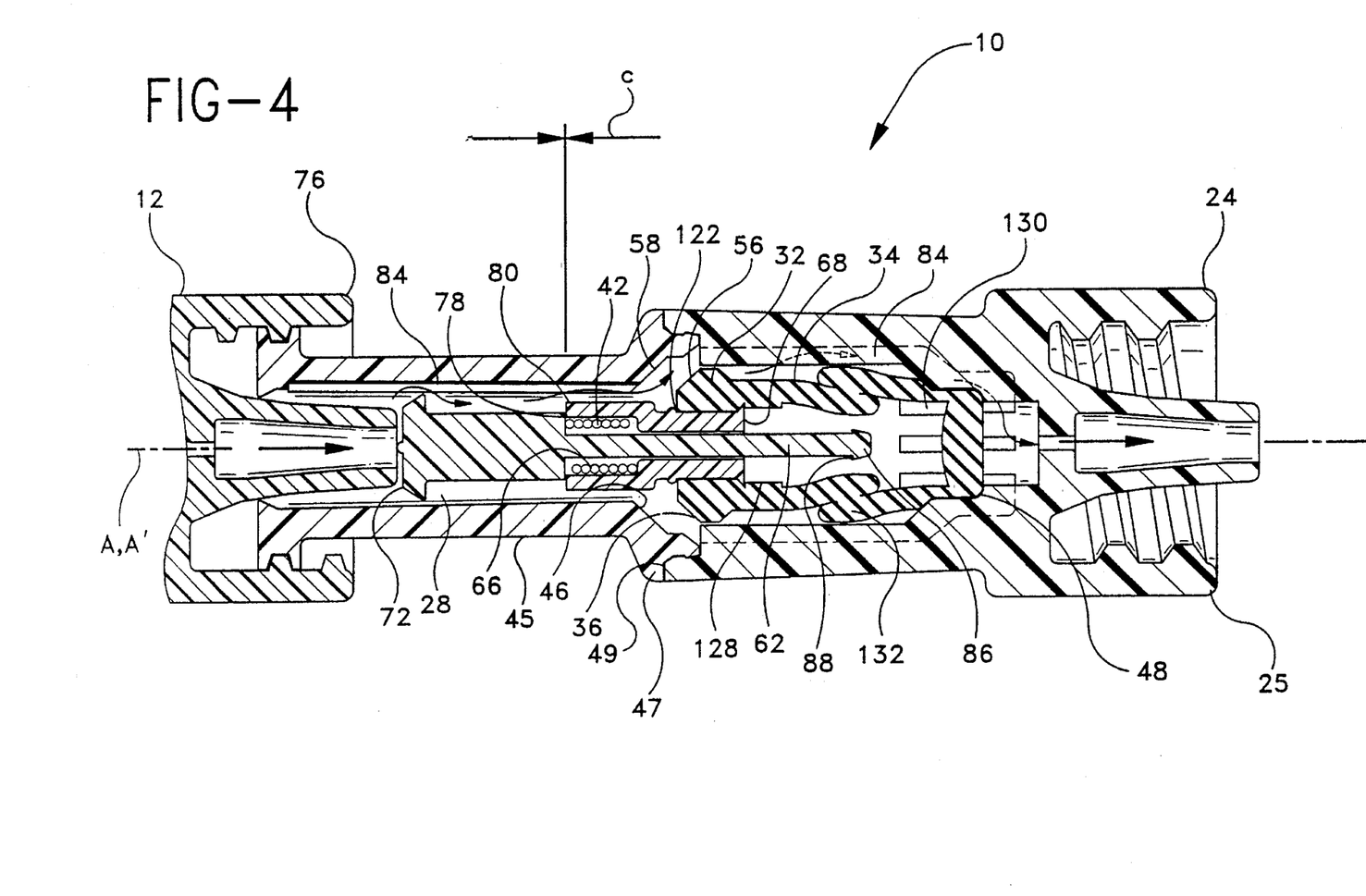
FIG. 4 is a schematic cross-sectional view from FIG. 3 with the fluid handling device fully mounted.
Figure 5:
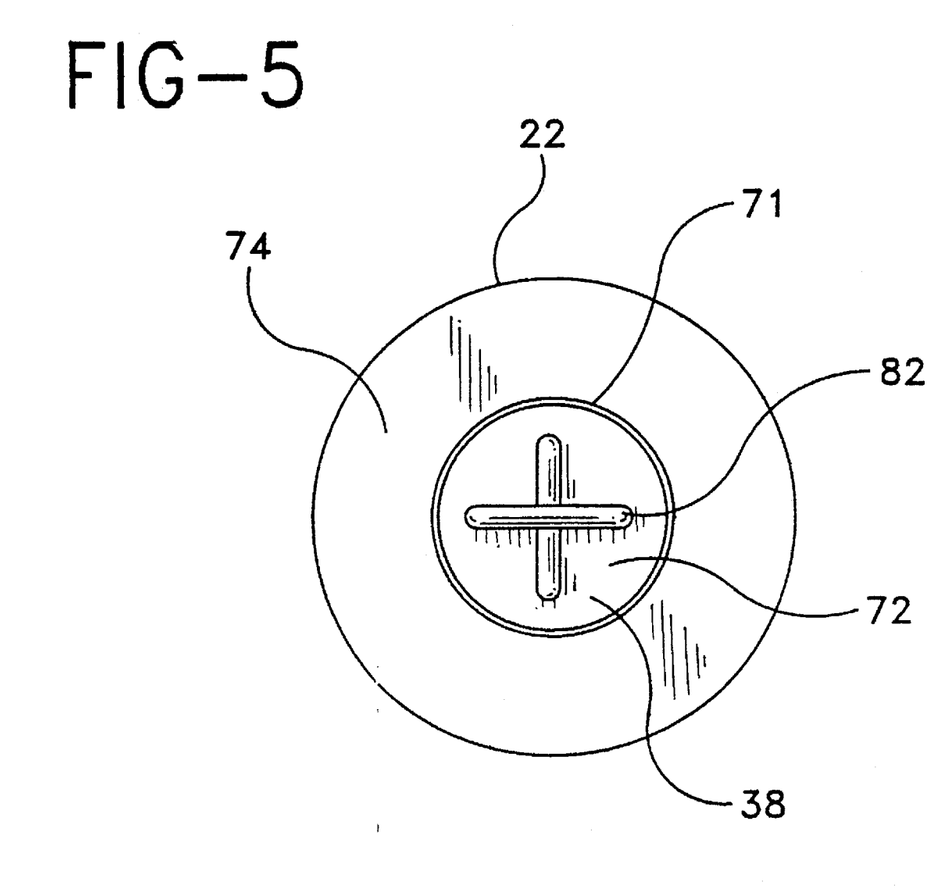
FIG. 5 is a end view of the embodiment of FIG. 1.

Adapter 10 includes a valve 32 contained within chamber 30 for selectively obstructing and allowing fluid flow through passageway 28. Valve 32 preferably includes an elongate resilient member 34 with a proximal end 36 and a longitudinal axis A' substantially coaxial to axis A of the body. Valve 32 is preferably normally closed as illustrated in FIGS. 2 and 3, and has an open position as illustrated in FIG. 4. Valve 32 preferably further includes a pusher 38 at proximal end 36 of the resilient member. Pusher 38 preferably includes a telescopic portion 40 located at proximal end 36 of the elongate resilient member. Preferably telescopic portion 40 has an extended position illustrated as distance "e" in FIG. 2 and a collapsed position shown as distance "c" shown in FIG. 4. Telescopic portion 40 is preferably biased to the extended position by a coil spring 42, In the preferred embodiment, passageway 28 has an inside surface 44 having a proximal shoulder 46 and a distal shoulder 48 projecting inwardly defining chamber 30. Preferably, body 16 is substantially cylindrical and includes a proximal section 45 and a distal section 47 joined at a parting line 49 intermediate proximal shoulder 46 and distal shoulder 48. Distal shoulder 48 is preferably formed from a plurality of segments 50 having openings 52 between the segments. Valve 32 preferably forms a fluid tight seal 54 using a chamfered surface 56 on proximal end 36 of the resilient member to engage a frusto-conical surface 58 on proximal shoulder 46. Preferably, resilient member 34 is axially compressed between proximal shoulder 46 and distal shoulder 48 biasing valve 32 to the normally closed position.

Pusher 38 serves to move valve 32 to the open position by displacing the resilient member proximal end 36 from surface 58 on the proximal shoulder. Preferred pusher 38 includes a proximal portion 60 with a rod 62 projecting axially distally having coil spring 42 longitudinally placed therearound The preferred pusher further includes a distal portion 64 with a receptacle 66 and an opening 6g therethrough Rod 62 is positioned for axial slidable movement through opening 68, forming telescopic portion 40. The extremes of the slidable movement of rod 62 through opening 68 define the extended position and the collapsed position of telescopic portion 40.

Preferred pusher 38 also includes a proximal extension 70 having a proximal surface 72 disposed so that when telescopic portion 40 is in the extended position, proximal surface 72 forms a substantially continuous surface with a proximal surface 74 of female luer fitting 22. Surface 74 also includes an opening 75 therethrough. Since pusher 38 forms a substantially continuous proximal surface with female luer proximal surface 74, the preferred adapter may be wiped substantially clean by an operator when no fluid delivery device is present.

In the preferred adapter 107 the present invention is intended to encompass several embodiments of an interface 71 between female luer proximal surface 74 and pusher proximal surface 72 at opening 75 as illustrated in FIGS. 2 and 6a–c.

Figure 6A:
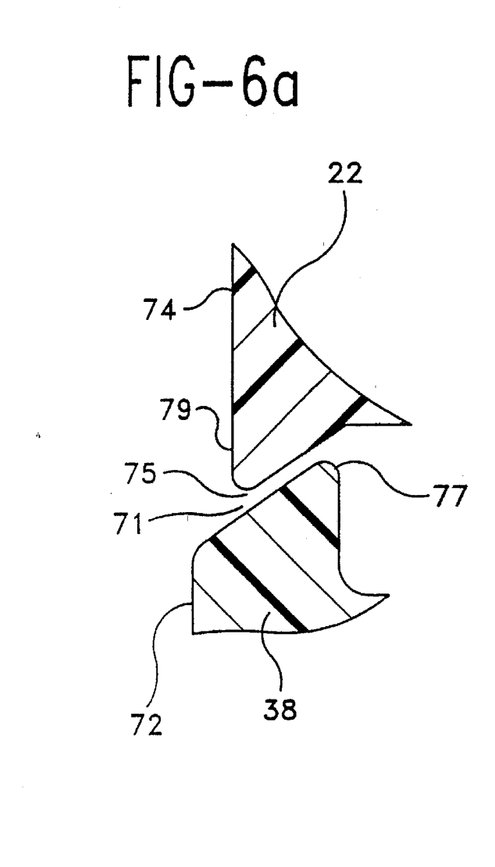
FIG. 6a is an enlarged cross-sectional detail from FIG. 2 showing a portion of the proximal end.
Figure 6B:
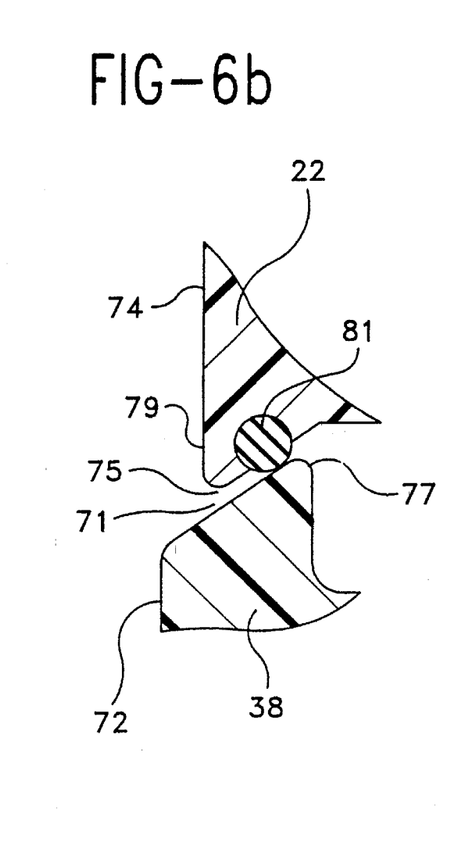
Figure 6C:
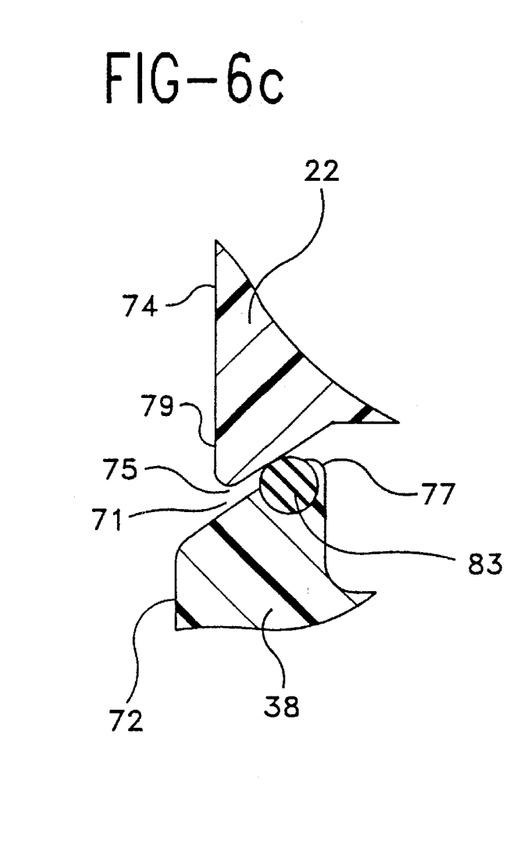

In one embodiment of interface 71, opening 75 preferably includes a lip 79 extending inwardly to contact a shoulder 77 on the pusher proximal extension substantially closing opening 75. The contact between lip 79 and shoulder 77 provides the substantially continuous proximal surface of the adapter to facilitate wiping the proximal surface when the telescopic portion is in the extended position as shown in FIG. 6a. An alternate embodiment of interface 71 includes providing lip 79 with a resilient gasket 81 to contact shoulder 77 and substantially close opening 75 as shown in FIG. 6b. Another alternate embodiment of interface 71 includes providing shoulder 77 of the pusher proximal extension with a resilient gasket 83 to contact lip 79 as shown in FIG. 6c.

Referring to FIGS. 3 and 4, when a fluid handling device 12 having a male luer fitting 76 is mounted onto the preferred adapter, male luer fitting 76 preferably contacts proximal surface 72 and displaces pusher telescopic portion 40 from the extended position to the collapsed position by overcoming the bias provided by coil spring 42. When the pusher telescopic portion is collapsed, a distal end 78 of the pusher proximal portion contacts a proximal end 80 of receptacle 66 substantially containing spring 42 within receptacle 66. As male luer 76 is fully mounted on female luer 22, collapsed pusher 38 displaces proximal end 36 of the resilient member and displaces chamfered surface 56 from frusto-conical surface 58 thereby opening valve 32. Pusher proximal surface 72 preferably includes a proximally projecting protuberance 82, shown as a cross in FIG. 1, to prevent adherence of the male luer fitting to the pusher proximal surface and to facilitate fluid flow from the fluid handling device into the adapter. Other shapes for protuberance 82 that would prevent the adherence of the male luer fitting to the pusher proximal surface and allow flow would also be satisfactory. Passageway 28 preferably includes at least one flow channel 84 for facilitating fluid flow from fluid handling device 12 through the adapter when valve 32 is open by providing a substantially continuous path, indicated by arrows in FIG. 4, for fluid flow.

Preferred adapter 10, by having a pusher with a telescopic portion, substantially eliminates the tendency, seen in many previous valved adapters, to spurt any liquid present in the passageway of the adapter as the fluid handling device is removed. As is seen in FIG. 3 for the preferred adapter 10, telescopic portion 40 allows male luer fitting 12 to substantially obstruct passageway 28 while valve 32 is fully closed. Telescopic portion 40 also allows the user to more easily control the dismounting of the fluid handing device to return adapter 10 to the state shown in FIG. 2. Since valve 32 of the adapter is already fully closed before the device is fully removed, there is little probability of backflow leakage through the adapter. Additionally, when any adapter is used to connect a syringe to a catheter in a blood vessel and the contents of the syringe are expelled, a continuous liquid column exists from the syringe to the open end of the catheter in the blood vessel. When the syringe is removed, if an adapter of the prior art were in use, the volume of the liquid column present in the syringe tip is removed from the column resulting in a like volume of blood being drawn back into the catheter. This "backflow" blood may clot and cause blockage in a subsequent use of the catheter. In the adapter of the present invention with the telescopic pusher, only a small proximal movement of the elongate resilient member is required to close valve 32. The balance of the volume of the liquid column in the syringe tip proximal to the valve seal is blocked by closure of valve 32 before the fluid handling device is fully removed from the flow path thus substantially eliminating the backflow of blood into the catheter.

Referring to FIGS. 2, 3 and 4, preferred rod 62 has a distal end portion 86 that serves as a ratchet 88 to allow distal passage of rod 62 through opening 68, when adapter 10 is being assembled. Ratchet 88 resists proximal movement through opening 68 thereby limiting the travel of the pusher proximal surface 72 to form the substantially continuous surface with proximal surface 74 of the female luer fitting.

Again referring to FIGS. 2, 3 and 4 preferred elongate resilient member 34 includes an elongate cavity 120 with an open end 122 at proximal end 36 of the resilient member. Cavity 120 is preferably substantially coaxial to axis A' of the member. Preferably cavity 120 has an internal surface 126 having a plurality of inward proximal projections 128 and distal ribs 130. Proximal projections 128 serve to retain pusher 38 at proximal end 36 of the resilient member. Additionally, proximal projections 128, in conjunction with distal ribs 130, as shown in FIG. 4, define a region of collapse 132 for the resilient member. When resilient member 34 is further axially compressed by displacing chamfered surface 56 from frusto-conical surface 58, the resilient member compresses by collapsing in region 132 thereby minimizing the effect of the resilient member on fluid flow through flow channel 84. Additionally, for the embodiment of adapter 10 shown in FIGS. 1–6, cavity 120 provides clearance for rod 62 when telescopic portion 40 is displaced from the extended position to the collapsed position.

Elongate resilient member 34 may be formed from materials such as natural rubber, chloroprene, silicone rubber and ethylene-propylene-diene-monomer (EPDM) or other similar resilient materials. Preferably, elongate resilient member 34 is formed from silicone rubber having a durometer between about 30 to about 80 Shore A.

In the interest of simplifying the present disclosure all examples of the present invention show distal end 24 of the preferred adapter as a male luer fitting 25. It is intended that other applications, e.g., where distal end 24 attaches to a catheter, feeding tube or medical devices other than a female luer fitting, are within the scope of the present invention.

The compression of elongate resilient member 34 to open valve 32 allows for repeated cycles of mounting and dismounting fluid handling devices with reliable opening and closing of the valve. Additionally, the elongate resilient member allows the adapter of the present invention to be tolerant of male luer fittings at the extremes of the allowable tolerance in length and diameter provided by the international standard. This tolerance is provided by the ability of the elongate resilient member to collapse about cavity 120 in the region of collapse. Once valve 32 is fully opened, additional axial distal displacement of proximal end 36 of the resilient member may be absorbed by the collapse in region 132 without causing obstruction fluid flow in channel 84.

The resilient gaskets 81 and 83 of the embodiments of FIGS. 6b and 6c used at interface 71 between the pusher proximal surface 72 and the female luer fitting surface 74 may be formed from natural rubber, chloroprene silicone rubber, EPDM and the like. Preferably, the gaskets are formed from silicone rubber having a durometer between about 30 and about 80 Shore A.

Thermoplastic resins such as polyethylene, polycarbonate, polyacrylate, polyester, polyacetal, polyamide, polypropylene, polysulfone, polyvinylchloride, polystyrene, acrylonitrile-butadiene-styrene (ABS) and the like are suitable for forming pusher 38. Alternatively, pusher 38 may be formed from stainless steel. Preferably, the pusher is formed from polypropylene.

Body 16 may be formed from resins such as polystyrene, polyester, polyacrylate, polypropylene, polycarbonate, polytetrafluoroethylene, polysulfone, polyacetal, polyamide, polyvinyl chloride, ABS and the like. Preferably, body 16 is formed from polyester. Proximal section 45 and distal section 47 may be joined at parting line 49 by techniques such as solvent bonding, thermal welding, ultrasonic welding, snap-fit or other methods used for joining thermoplastic parts. Preferably, ultrasonic welding is used for joining body proximal section 45 to body distal section 47.

Figure 7:
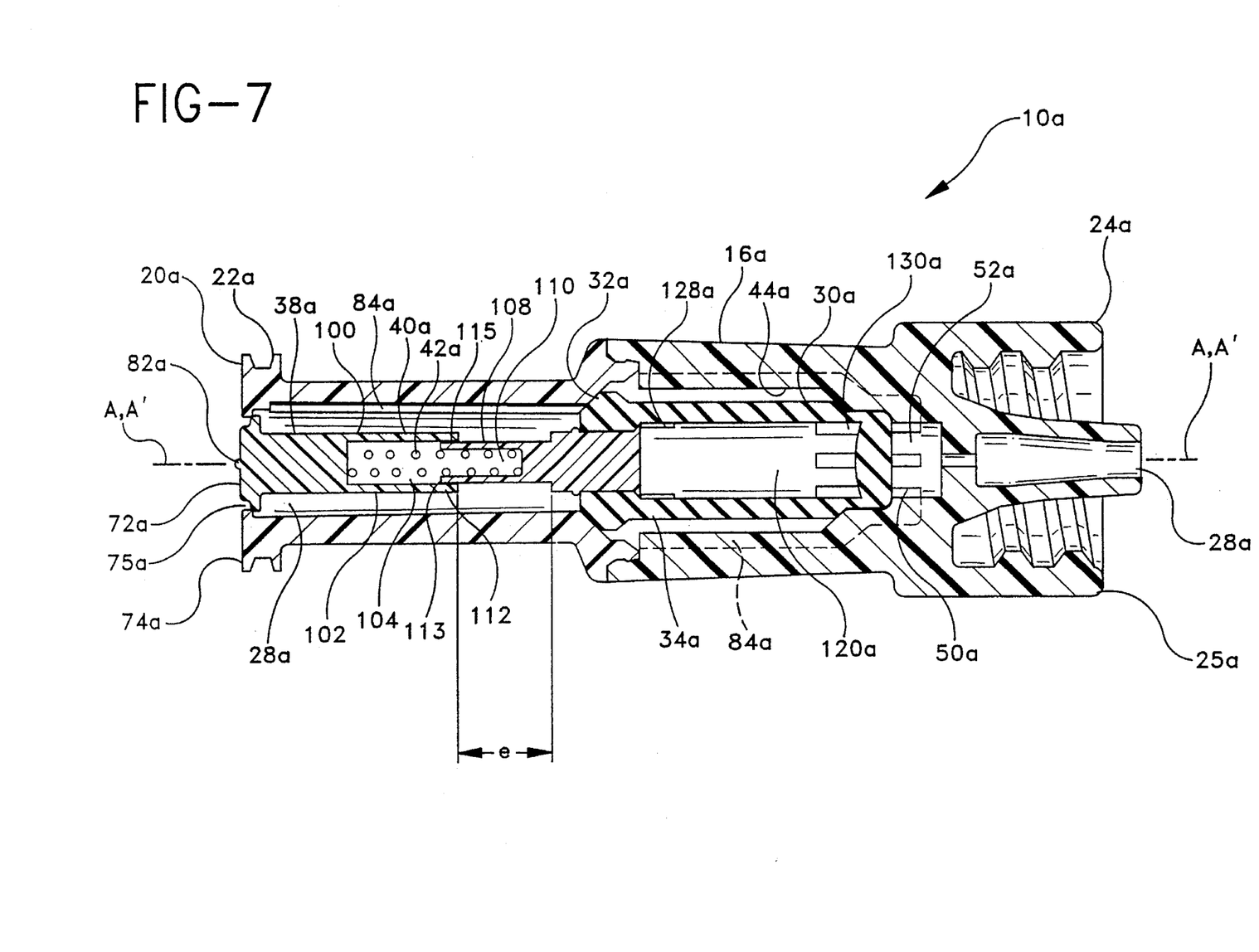
FIG. 7 is a schematic cross-sectional view of an alternate embodiment of the present invention analogous to the view of FIG. 2.
Figure 8:
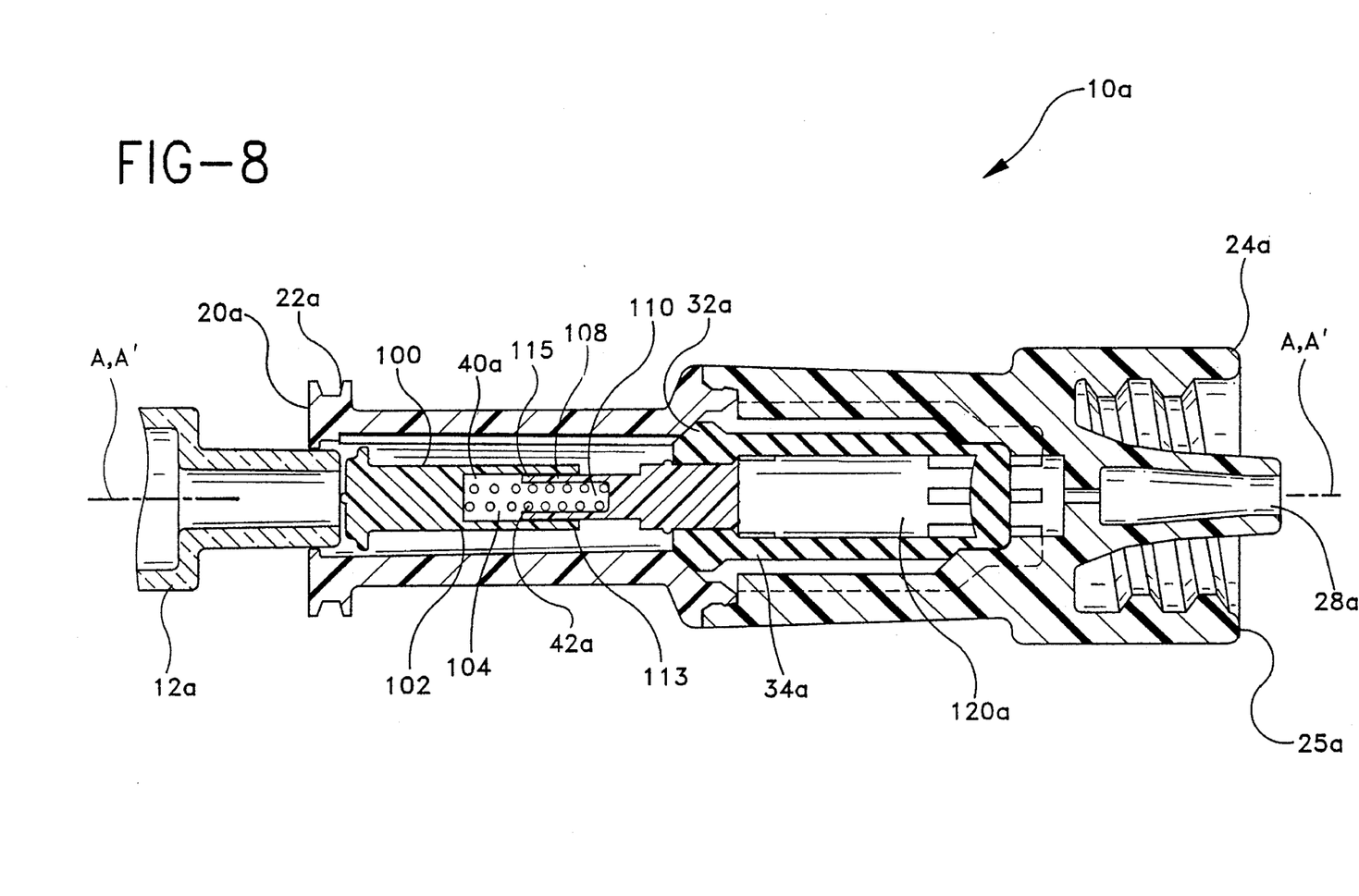
FIG. 8 is a schematic cross-sectional view of the embodiment of FIG. 7 with a fluid handling device partially mounted.
Figure 9:
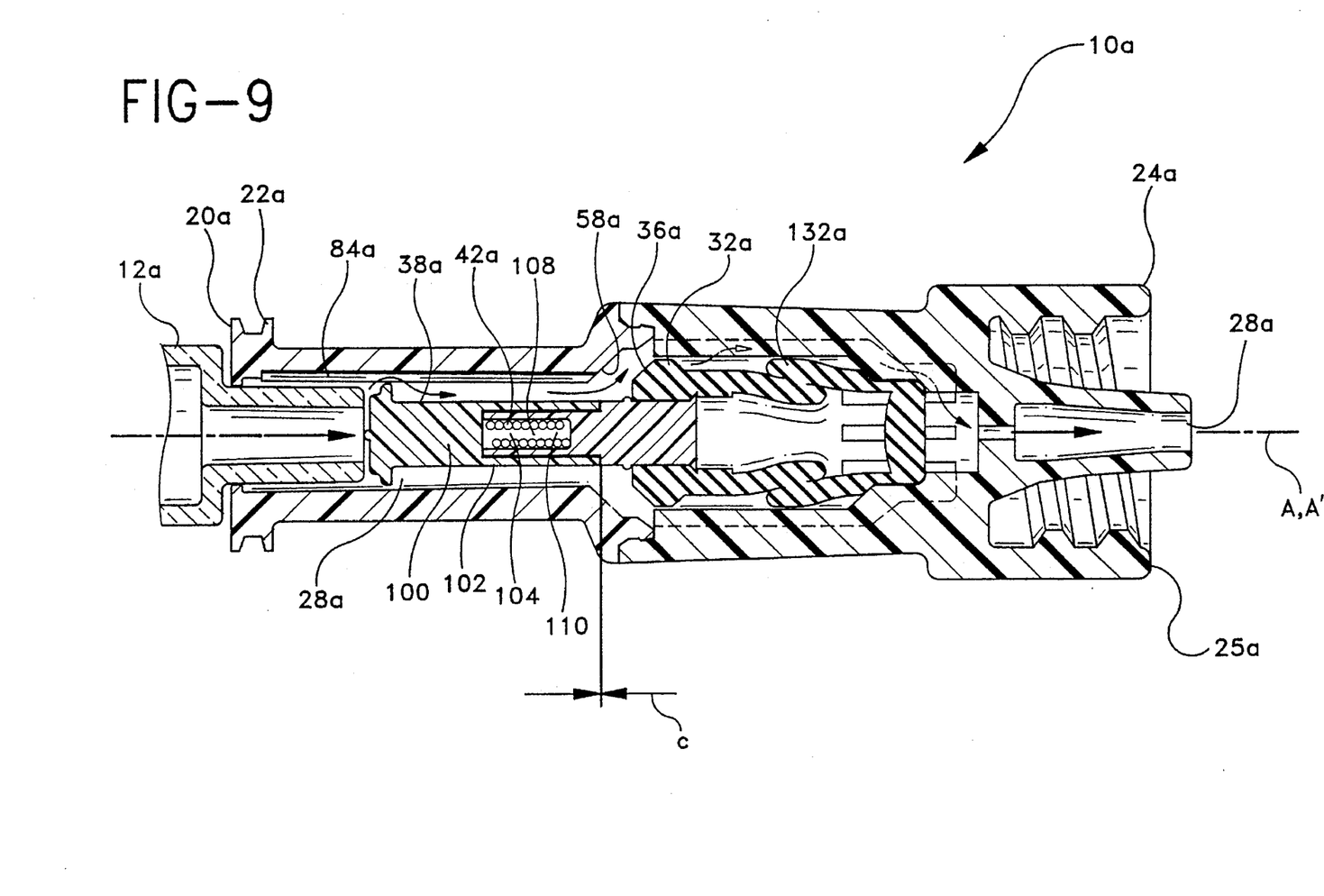
FIG. 9 is a schematic cross-sectional view of the embodiment of FIG. 7 with the fluid handling device fully mounted.

Referring to FIGS. 7, 8 and 9, an alternative embodiment of the adapter of the present invention is illustrated. In this alternative embodiment, the structure of the adapter is substantially similar to the adapter of the embodiments of FIGS. 1-6. Accordingly, substantially similar components that perform substantially similar functions will be numbered identically to those components of the embodiments of FIGS. 1-6 except that a suffix "a" is used to identify those components in FIGS. 7-9.

Pusher 38a serves to move valve 32a to the opened position by displacing proximal end 36a from surface 58a on the proximal shoulder. In this embodiment preferred pusher 38a includes a proximal portion 100. Proximal portion 100 preferably includes a first hollow sleeve portion 102 having a first well 104 therein. Pusher 38a preferably also includes a distal portion 106 with a second hollow sleeve portion 108 having a second well 110 therein. In this embodiment, telescopic portion 40a preferably includes second hollow sleeve portion 108 being fit within first hollow sleeve portion 102 for axial slidable movement between the extended position as shown in FIG. 7 and the collapsed position as shown in FIG. 9. Coil spring 42a is preferably fit within the first and second wells for biasing pusher telescopic portion 40a to the extended position. Preferably, the first sleeve portion and the second sleeve portion include a ratchet 112 to retain the distal portion within the proximal portion when the pusher telescopic portion is in the extended position. Ratchet 112 preferably includes interlocking protuberances 113 and 115 which serve to limit the travel of the travel of the telescopic portion. Pusher proximal surface 72a preferably forms a substantially continuous surface with proximal surface 74a of female luer fitting 22a when telescopic portion 40a is in the extended position.

Figure 10A:
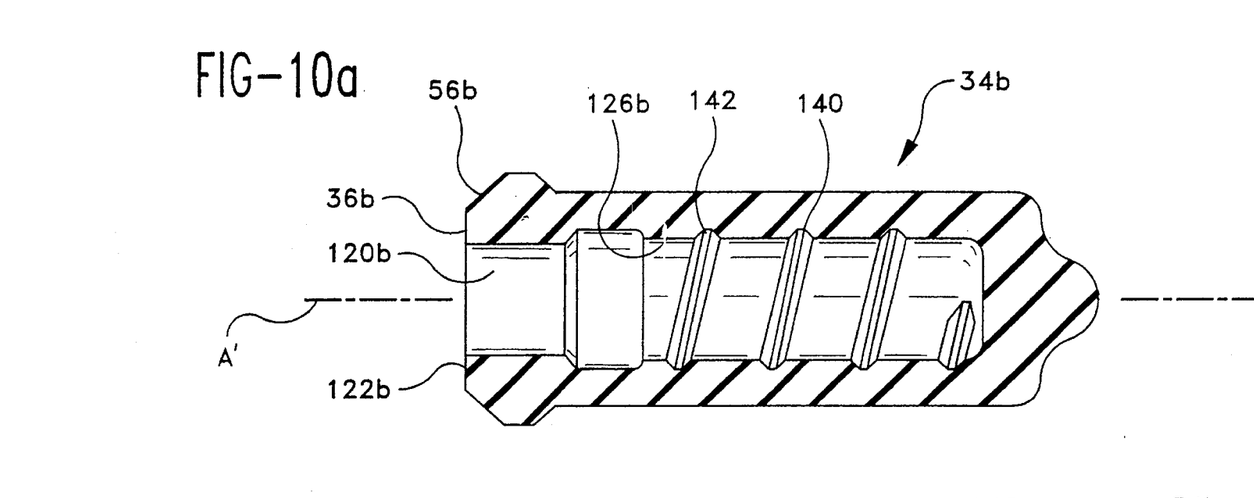
FIG. 10a is a longitudinal cross-sectional view of another embodiment of the elongate resilient member analogous to the view of the member shown in FIG. 3.
Figure 10B:
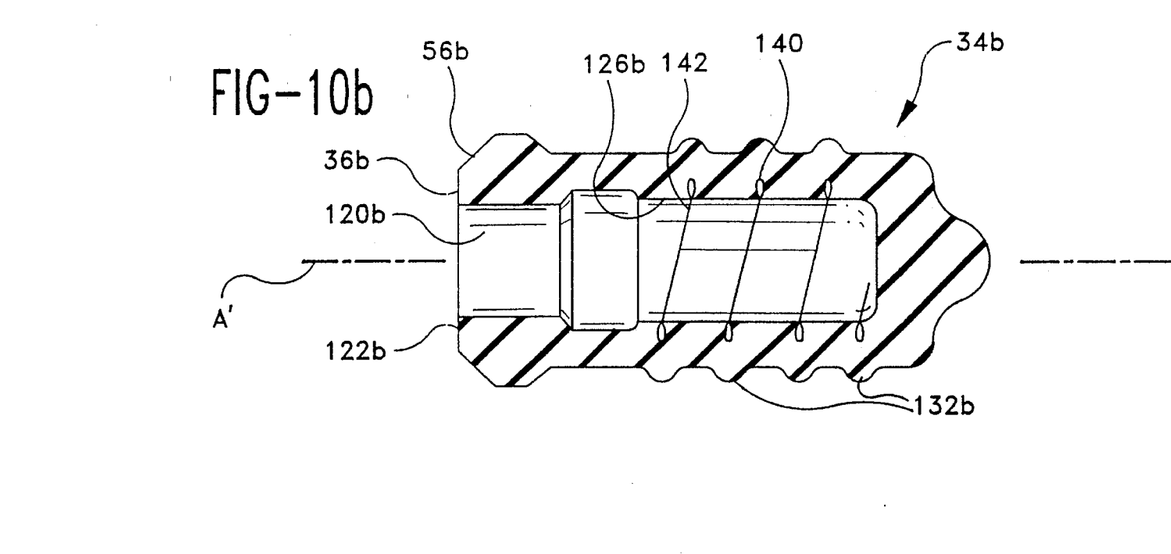
FIG. 10b is a longitudinal cross-sectional view of the embodiment of FIG. 10a analogous to the view of the member shown in FIG. 4.

Referring to FIGS. 10a and 10b, another embodiment of the elongate resilient member of the adapter of the present invention is illustrated. In this embodiment of the elongate resilient member the structure of the adapter itself and the function of the elongate resilient member is substantially similar to the embodiments of FIGS. 1-9. Accordingly, substantially similar components performing substantially similar functions are numbered identically except that a suffix "b" is used for those components in FIGS. 10a and 10b.

As shown in FIGS. 10a and 10b elongate resilient member 34b includes an elongate cavity 120b with and open end 122b at proximal end 36b of the resilient member. Preferably, cavity 120b has an internal surface 126b with at least one depression 140 in the form of groove 142 therein. Depression 140 may be in the form of spiral groove 142 as shown in FIGS. 10a and 10b, but a spaced series of circular depressions coaxially disposed to axis A' or other shaped depressions and the like is considered to be within the scope of the invention. Depression 140 serves to direct the collapse of the elongate member 34b into at least one region of collapse 132b. In this embodiment, the region of collapse 132b is well controlled as seen in FIG. 10b causing substantially no interference with fluid flow through the adapter when the valve is opened. The tolerance of variation in engagement lengths of male luers mounted on the adapter is retained.

The adapter of the present invention provides users with an easy-to-use valved attachment for a variety of medical devices that is easy to wipe clean and that substantially prevents uncontrolled fluid discharges. The valved adapter is capable of withstanding multiple cycles of mounting and dismounting fluid handling devices without substantial degradation of the valve's sealing ability.

What is claimed is:

1. A valved adapter for connecting a fluid handling device to a medical device comprising:

a body with a longitudinal axis and having a proximal end comprising a female luer fitting, a distal end and a passageway therethrough, said passageway having a chamber intermediate said distal end and said proximal end;

a valve contained within said chamber in a normally closed position but being operative to an open position, said valve comprising a relatively elongate resilient member having a proximal end and an axis substantially coaxial to said longitudinal axis, said resilient member being axially compressed in said chamber thereby biasing said valve to said normally closed position and said valve further comprising a pusher disposed at said proximal end of said elongate resilient member, said pusher adapted to selectively displace said valve from said normally closed position to said open position, said pusher having a telescopic portion having an extended position and a collapsed position, said telescopic portion being biased to said extended position, and, said pusher being disposed to operate said valve to said open position only when said pusher is in said collapsed position.

2. The valved adapter of claim 1 wherein said female luer fitting comprises a proximal surface and a proximal opening for accepting a male luer fitting, and said pusher further comprises a proximal projection having a proximal surface so that when said telescopic portion is in said extended position, said pusher proximal surface forms a substantially continuous surface with said surface of said female luer fitting at said opening.

3. The valved adapter of claim 2 wherein said proximal opening further comprises a lip and said pusher proximal portion comprises a shoulder for contacting said lip when said telescopic portion is in said extended position.

4. The valved adapter of claim 3 wherein said lip further comprises a resilient gasket for mating with said pusher shoulder, thereby substantially closing said opening when said telescopic portion is in said extended position.

5. The valved adapter of claim 3 wherein said pusher shoulder further comprises a resilient gasket for contacting said lip, thereby substantially closing said opening when said telescopic portion is in said extended position.

6. The valved adapter of claim 2 wherein said pusher proximal surface is disposed so that when a fluid handling device having the male luer fitting is being mounted on said female luer fitting, the male luer fitting contacts said pusher proximal surface displacing said pusher telescopic portion from said extended position to said collapsed position.

7. The valved adapter of claim 2 wherein said pusher proximal surface further comprises a protuberance projecting proximally to facilitate fluid flow from the male luer fitting.

8. The valved adapter of claim 2 wherein said telescopic portion is biased to said extended position by a coil spring and wherein a force for overcoming said bias of said telescopic portion is less than a force for overcoming said valve bias.

9. The valved adapter of claim 8 wherein said telescopic portion comprises a proximal portion including a rod portion having said coil spring therearound and a distal portion including a receptacle portion having an opening therethrough, said rod being positioned for axial slidable movement through said opening, said slidable movement causing said displacement of said telescopic portion from said extended position and said collapsed position;

wherein when the male luer fitting is being mounted on said female luer fitting the male luer fitting contacts said pusher and displaces said pusher to said collapsed position so that said spring is contained within said receptacle, further compresses said elongate resilient member and thereby allows fluid flow when said male luer fitting is fully mounted; and wherein when the male luer fitting is being dismounted from said female luer fitting the male luer fitting contacts said pusher so that said telescopic portion remains in said collapsed position and thereby allows said valve to return to said normally closed position before the male luer is fully dismounted from said female luer fitting, substantially preventing fluid discharge from said adapter as said valve returns to said normally closed position, said telescopic portion being returned to said extended position when the male luer fitting is fully dismounted.

10. The valved adapter of claim 9 wherein said rod has a distal end portion including a ratchet that allows an initial distal movement of said rod into said opening during assembly of said adapter, said ratchet opposing a proximal movement of said proximal end portion of said rod through said opening, thereby providing a limit to said extended position of said telescopic portion and retaining said pusher proximal portion in said adapter.

11. The valved adapter of claim 8 wherein said pusher comprises a proximal portion including a first hollow sleeve portion having a first well therein and a distal portion including a second hollow sleeve portion having a second well therein, and said telescoping portion comprises said second hollow sleeve portion being fit within said first hollow sleeve portion for slidable axial motion between said extended position and said collapsed position, with said coil spring being contained within the wells so that said coil spring biases said telescopic portion to said extended position, said first sleeve portion and said second sleeve portion including a ratchet to retain said second portion within said first portion thereby providing a limit to said extended position and retaining said pusher proximal portion in said adapter.

12. The adapter of claim 8 wherein said pusher is formed from a material selected from the group consisting of stainless steel, and the resins polyethylene, polycarbonate, polyacrylate, polyacetal, polyamide, polypropylene, polysulfone, polyvinylchloride, polystyrene and acrylonitrile-butadiene-styrene.

13. The valved adapter of claim 1 wherein said passageway further comprises an inside surface having a proximal shoulder and a segmented distal shoulder projecting inwardly from said surface of said passageway, said shoulders defining said chamber, said distal shoulder having openings therethrough between said segments; and said inside surface further comprising at least one flow channel to facilitate fluid through said passageway by providing a continuous passageway when said valve is in said open position.

14. The valved adapter of claim 13 wherein said valve further comprises said elongate resilient member being axially compressed between said proximal shoulder and said distal shoulder so that said proximal end of said elongate resilient member forms a fluid tight seal with said proximal shoulder.

15. The valved adapter of claim 14 wherein said elongate resilient member further comprises a cavity having an open end at said proximal end of said member substantially coaxial to said axis of said member and having a plurality of inward proximal projections and distal ribs, said proximal projections serving to retain said pusher at said proximal end of said member, and in conjunction with said distal ribs, define a region of collapse when said resilient member is further axially compressed for opening said valve.

16. The adapter of claim 15 wherein said elongate resilient member is formed from a material having a durometer between about 30 and 80 Shore A selected from the group consisting of natural rubber, chloroprene, silicone rubber and ethylene-propylene-diene-monomer.

17. The valved adapter of claim 14 wherein said elongate resilient member further comprises a cavity having an inside surface substantially coaxial to said axis of said member, said cavity having at least one depression in said inside surface for providing at least one region of collapse when said resilient member is further axially compressed for opening said valve.

18. The valved adapter of claim 14 wherein said depression in said inside surface of said cavity comprises a spiral groove from said proximal end to said distal end.

19. The adapter of claim 14 wherein said body is substantially cylindrical and comprises a proximal section and a distal section joined at parting line intermediate said proximal shoulder and said distal shoulder, said body being formed from a resin selected from the group consisting of polystyrene, polycarbonate, polyacrylate, polypropylene, polyethylene, polytetrafluoroethylene, polysulfone, polyacetal, polyamide, polyvinylchloride and acrylonitrile butadiene styrene copolymer.

20. A valved adapter for connecting a fluid handling device to a medical device comprising:

a body with a longitudinal axis having a proximal end comprising a female luer fitting having a proximal surface with an opening for receiving a male luer fitting on a fluid handling device, a distal end and a passageway therethrough, said passageway having a chamber intermediate said proximal end and said distal end;

a valve contained within said chamber for selectively obstructing and allowing fluid flow through said passageway, said valve comprising a relatively elongate resilient member having an axis substantially coaxial to said longitudinal axis of said body, said resilient member being in an axial compression in said chamber thereby biasing said valve to a normally closed position and obstructing fluid flow;

said valve further comprising a pusher disposed on said elongate resilient member for contacting the male luer fitting of the fluid handing device when the male luer fitting is being mounted on and dismounted from said female luer fitting and for axially displacing and further axially compressing said resilient member thereby allowing fluid flow through said passageway, said pusher having a telescopic portion with an extended position and a collapsed position and being biased to said extended position where said pusher substantially occludes said passageway at said opening in said proximal end;

wherein when the male luer fitting is being mounted on said female luer fitting the male luer fitting contacts said pusher and displaces said telescopic portion to said collapsed position, further compresses said resilient member, and thereby allows fluid flow when the male luer fitting is fully mounted on said female luer fitting; and wherein when the male luer fitting is being dismounted from said female luer fitting the male luer fitting contacts said pusher so that said telescopic portion remains in said collapsed position and thereby allows said valve to return to said normally closed position before the male luer fitting is fully dismounted from the female luer fitting substantially preventing a fluid discharge from said adapter as the valve closes, said telescopic portion returning to said extended position when said male luer fitting is fully dismounted from said female luer fitting, and wherein a force for overcoming said bias of said telescopic portion is less than a force for overcoming said valve bias.

21. The valved adapter of claim 20 wherein said telescopic portion is biased to said extended position by a coil spring.

22. A valved adapter for connecting a fluid handling device to a medical device comprising:

a body with a longitudinal axis and having a proximal end comprising a female luer fitting, a distal end and a passageway therethrough, said passageway having a chamber intermediate said distal end and said proximal end;

a valve contained within said chamber in a normally closed position but being operative to an open position, said valve comprising a relatively elongate resilient member having a proximal end, an axis substantially coaxial to said longitudinal axis, said elongate resilient member having an axial cavity open at said proximal end and an inside surface having a depression therein extending distally spirally from said proximal end, said depression defining a region of collapse of said elongate resilient member when said member is further axially compressed: and said valve further comprising a pusher disposed at said proximal end of said elongate resilient member, said pusher having a telescopic portion having an extended position and a collapsed position, said telescopic portion being biased to said extended position.

* * * * *